(12) United States Patent
Miller

(10) Patent No.: US 10,583,027 B2
(45) Date of Patent: Mar. 10, 2020

(54) ORTHOSIS WALKING BOOT

(71) Applicant: Orthomerica Products, Inc., Orlando, FL (US)

(72) Inventor: John Jeffrey Miller, Apopka, FL (US)

(73) Assignee: ORTHOMERICA PRODUCTS, INC., Orlando, FL (US)

( * ) Notice: Subject to any disclaimer, the term of this patent is extended or adjusted under 35 U.S.C. 154(b) by 806 days.

(21) Appl. No.: 15/236,206

(22) Filed: Aug. 12, 2016

(65) Prior Publication Data
US 2017/0056230 A1 Mar. 2, 2017

Related U.S. Application Data

(60) Provisional application No. 62/211,517, filed on Aug. 28, 2015.

(51) Int. Cl.
*A61F 5/01* (2006.01)
*A61F 5/30* (2006.01)

(52) U.S. Cl.
CPC .............. *A61F 5/0111* (2013.01); *A61F 5/30* (2013.01)

(58) Field of Classification Search
CPC .... A61F 5/0111; A61F 5/0195; A61F 5/0127; A61F 5/30
USPC .......................................................... 602/23
See application file for complete search history.

(56) References Cited

U.S. PATENT DOCUMENTS

| | | | | |
|---|---|---|---|---|
| 3,955,565 A * | 5/1976 | Johnson, Jr. ........ | A61F 5/05816 602/12 |
| 4,057,056 A * | 11/1977 | Payton .................. | A61F 5/0585 602/11 |
| 5,527,269 A * | 6/1996 | Reithofer .............. | A61F 5/0111 602/27 |
| 5,833,639 A * | 11/1998 | Nunes ................... | A61F 5/0111 602/23 |
| 6,361,514 B1 | 3/2002 | Brown et al. | |
| 2002/0128574 A1 * | 9/2002 | Darby .................. | A61F 5/0111 602/23 |

(Continued)

FOREIGN PATENT DOCUMENTS

WO WO 97/36507 10/1997
WO WO-9736507 A1 * 10/1997 ............... A43B 7/00

OTHER PUBLICATIONS

International Search Report and Written Opinion dated Nov. 17, 2016 for Corresponding PCT/US2016/047045, Filed on Aug. 15, 2016 (11 pages).

(Continued)

*Primary Examiner* — Tarla R Patel

(57) ABSTRACT

An orthosis walking boot includes a posterior plastic shell with an open foot supporting portion extending outward from an integral open vertical leg extension to support a user's foot and leg and an anterior plastic shell with a horizontal foot covering portion for overlapping and covering the open foot supporting portion of the posterior shell and an integral open vertical leg extension for positioning within the posterior open vertical leg extension of the posterior shell. A two layer foam posterior liner extends upward within the posterior shell open vertical leg extension to receive the user's leg and adjustable fastening units secure the anterior shell to the posterior shell. An alternative orthosis walking boot with integrally attached foam liners on the posterior plastic shell and the anterior plastic shell is provided.

14 Claims, 8 Drawing Sheets

(56) References Cited

U.S. PATENT DOCUMENTS

2009/0287128 A1* 11/2009 Ingimundarson ..... A61F 5/0111
602/27
2010/0234782 A1* 9/2010 Hu ........................ A61F 5/0111
602/13
2014/0200492 A1* 7/2014 Ahlstrom .................. A61F 5/14
601/46

OTHER PUBLICATIONS

International Preliminary Report on Patentability dated Mar. 15, 2018 for Corresponding International Patent Application No. PCT/US2016/047045, filed Aug. 15, 2016.
Extended Supplementary European Search Report dated Aug. 16, 2018 for Corresponding European Patent Application No. 16842555.1, filed Jan. 26, 2018.

* cited by examiner

ORTHOSIS WALKING BOOT

CROSS-REFERENCE TO RELATED APPLICATIONS

This application claims priority to U.S. Provisional Application No. 62/211,517 filed on Aug. 28, 2015; the entire contents all of which are incorporated herein by reference.

BACKGROUND OF THE INVENTION

1. Field of the Invention

Charcot Syndrome, also known as Charcot Arthropathy, is a condition where patients lose sensations in the feet or ankles and may experience dislocations of bones and joints or fractures without injury or trauma, according to the American Orthopaedic Foot and Ankle Society. Patients with Charcot Syndrome experience increased warmth, swelling and redness in the feet and ankles. Fractures and dislocations that occur due to the condition can produce deformities of the feet or ankles which may affect the stability and flexibility of bones and joints.

Charcot foot is a serious condition that can lead to disfigurement, disability and amputation, according to the American College of Foot and Ankle Surgeons. As the condition advances, the joints crumble, and the foot adopts an abnormal appearance. Patients with diabetes, patients with long-term neuropathy, and neuropathic patients with tight Achilles tendons fall at risk of developing the condition and ought to take extra precaution and seek immediate treatment as soon as symptoms appear. Charcot can be a micro fracturing and dissolving of the bone commonly in the mid foot region.

2. Description of Related Art

Orthotics in the form of walking casts have attempted to protect the patient's foot while enabling the patient to still be mobile. The boot orthosis attempts to protect the patient's foot by encompassing it in plastic shells while accommodating any edema and reducing weight on the ankle/foot by trying to transfer it to the patient's leg and calf area by securing an anterior shell on the exterior of a posterior shell. Problems have occurred in trying to adjust the fit on the patient because of the potential of edema reduction as a result of a successful treatment and application of medication.

SUMMARY OF THE INVENTION

The orthosis walking boot utilizes a separate anterior shell with sufficient flexibility to overlap and cover a lower foot supporting portion of a stiffer posterior shell. A flexible split hinge on the anterior shell facilitates expansion and contraction movements of an anterior foot covering and the hinge divides the anterior foot covering from an anterior front vertical leg extension covering that extends upward and has an integral foam leg covering liner for contacting the user. The back of the posterior shell is configured to conform to a back calf or lower leg of the patient and has a rear oblong opening to provide a degree of flexibility and size adjustment with a heat gun of the posterior shell. The anterior front leg covering is configured to slide within the upward extension of the more rigid posterior shell, since the exterior of the anterior shell has a relatively rigid smooth plastic outer surface that will interface with and slide across an interior smooth plastic surface of the upward extension of the posterior shell.

The upward extension of the posterior shell surrounds an approximately U-shaped cross sectional foam liner that extends upward from a fixation at the heel of a foot portion of the posterior shell without a further fixation to the inner surface of the upward extension of the posterior shell. The foam posterior liner has a denser exterior layer for providing a support structure and a less dense interior foam layer for contacting the user. Accordingly, the foam posterior liner will bear directly against an outer side of the foam leg covering liner that is adhered to an interior surface of the anterior shell when inserted in the posterior shell.

An alternative arrangement of the upward extension of the posterior shell can have a U-shaped foam liner integrally attached to an interior of the upward extension of the posterior shell with the exterior of the anterior shell being directly against the foam liner of the upward extension of the posterior shell.

Appropriate flexible fastening straps are positioned with braces above the adjacent oblong opening and below the oblong opening and can be affixed to the patient's lower leg by bearing against the foam leg liner to reduce a portion of the patient's weight that would be bearing on the foot and thereby transform the weight bearing surfaces to the lower portion of the calf of the leg of the patient and an upper portion of the calf, to reduce the direct weight that must be borne by the bottom of the foot.

As a patient responds to a medical treatment of the Charcot Syndrome and the edema is reduced, the relatively flexible anterior shell can be appropriately adjusted in position and sized by the fastening to accommodate any reduction in the edema swelling while still maintaining a comfortable fit relative to the posterior shell to provide protection for the patient's foot and ankle.

Appropriate support braces are attached to the posterior shell to permit adjustment of the location of the anterior shell with the fastening straps to assure protection while permitting adjustment during treatment of the patient. Straps with a combination of hook and nap material such as provided with Velcro® products and their competitors can be secured through the support braces and to the front of the anterior shell.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
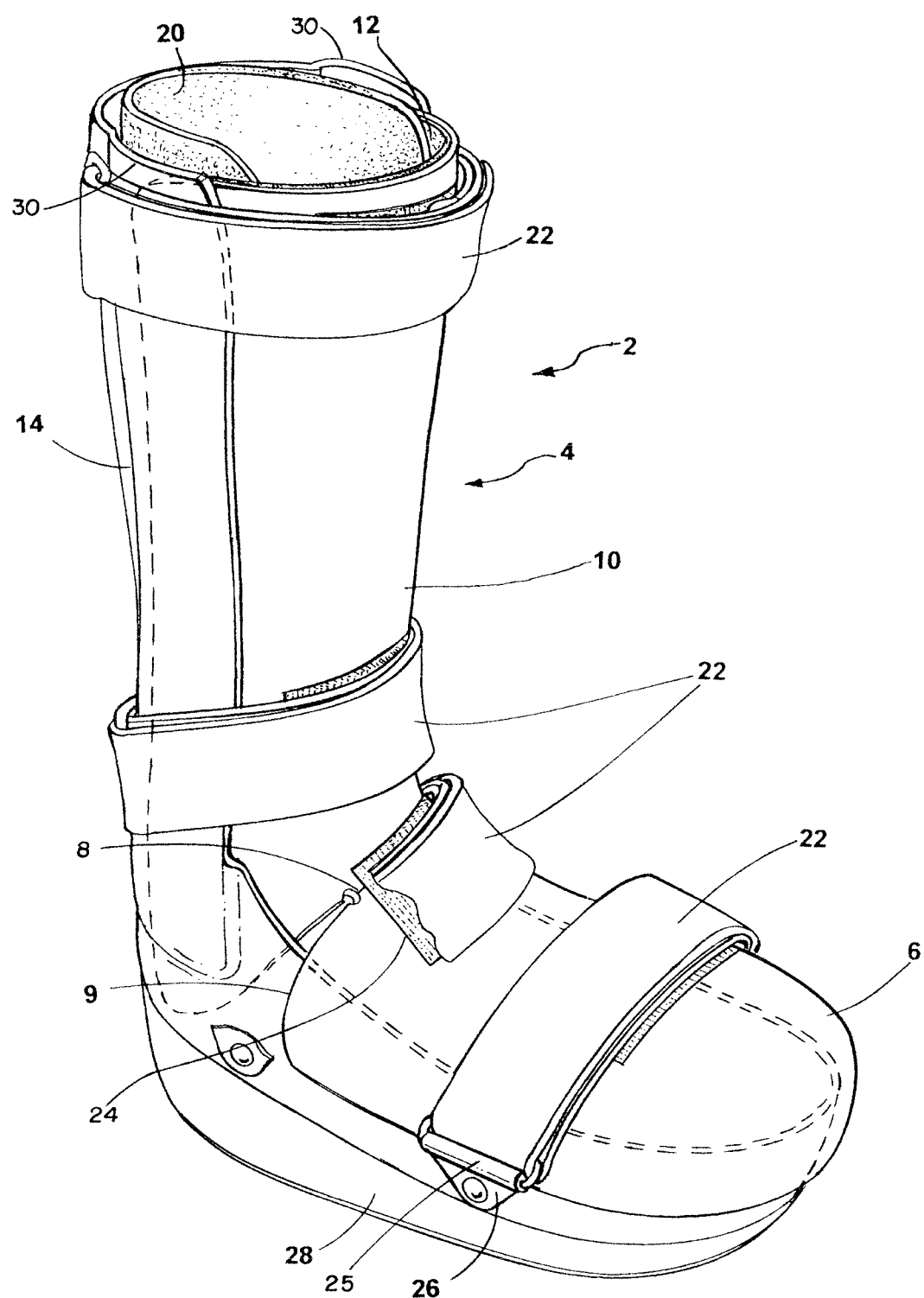
FIG. 1 is a perspective view of an assembled orthosis walking boot having the anterior shell fastened to the posterior shell with straps providing compression and positioning on the patient when tightened through braces.
Figure 3:
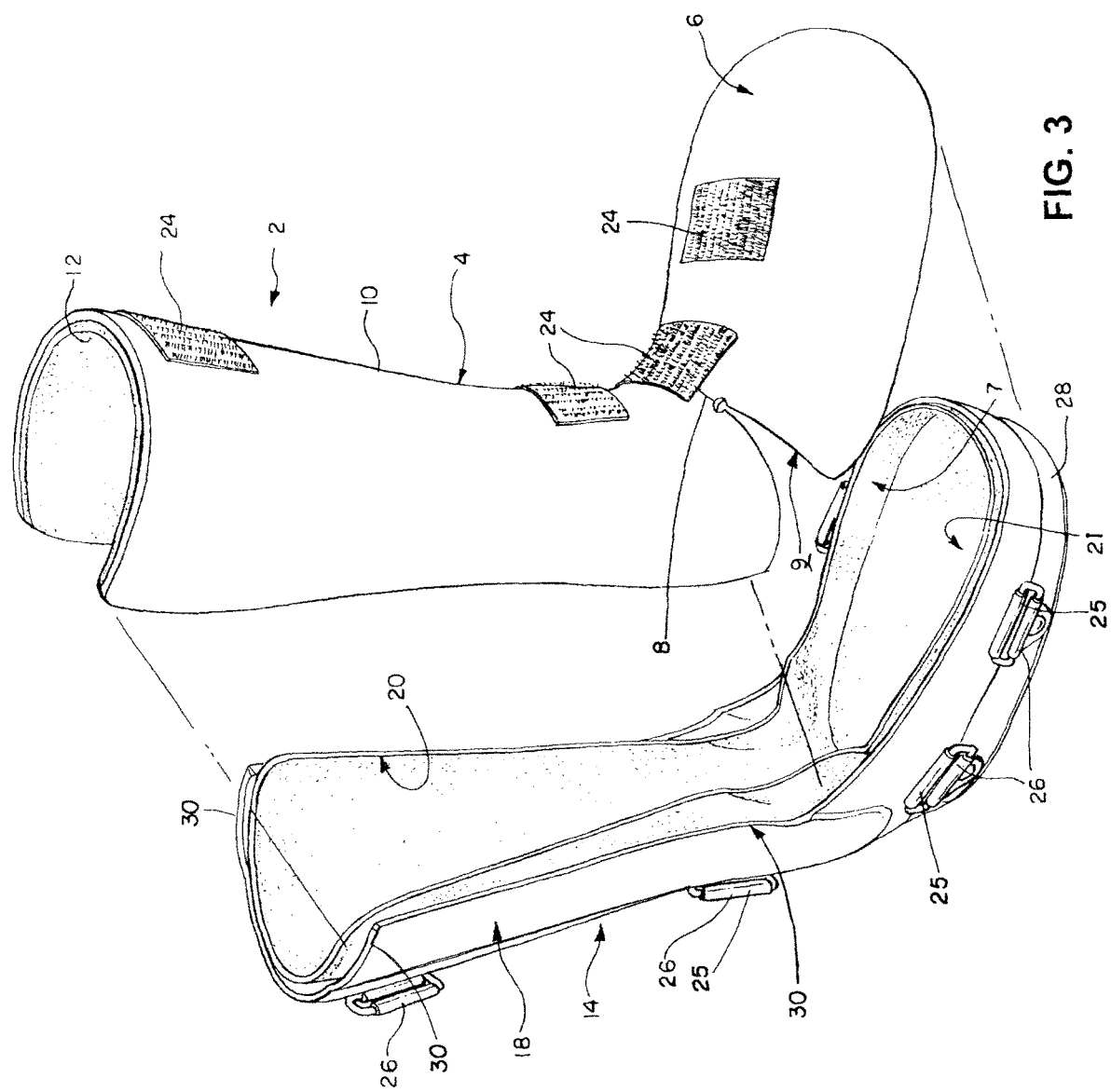
FIG. 3 is an exploded view of the orthosis walking boot disclosing the interior of the posterior shell and the exterior of the anterior shell.

Referring to FIG. 1, an orthosis walking boot 2 includes an anterior shell component 4 and a posterior shell component 14. The anterior shell 4 can be formed from a polypropylene plastic while the posterior shell 14 can also be formed from a thicker polypropylene plastic. The anterior shell 4 has an approximately L configuration with a lower anterior foot covering 6 and an upper front leg covering 10. A split hinge 8 extends across an upper surface of the anterior shell 4 to divide the front leg covering 10 from the anterior foot covering 6. As can be seen in FIGS. 1 and 3, a V opening 9 to the perimeter is provided on either side of the hinge 8 to facilitate adjustments and insertion of the front leg covering 10 into the posterior shell 14.

Figure 2:
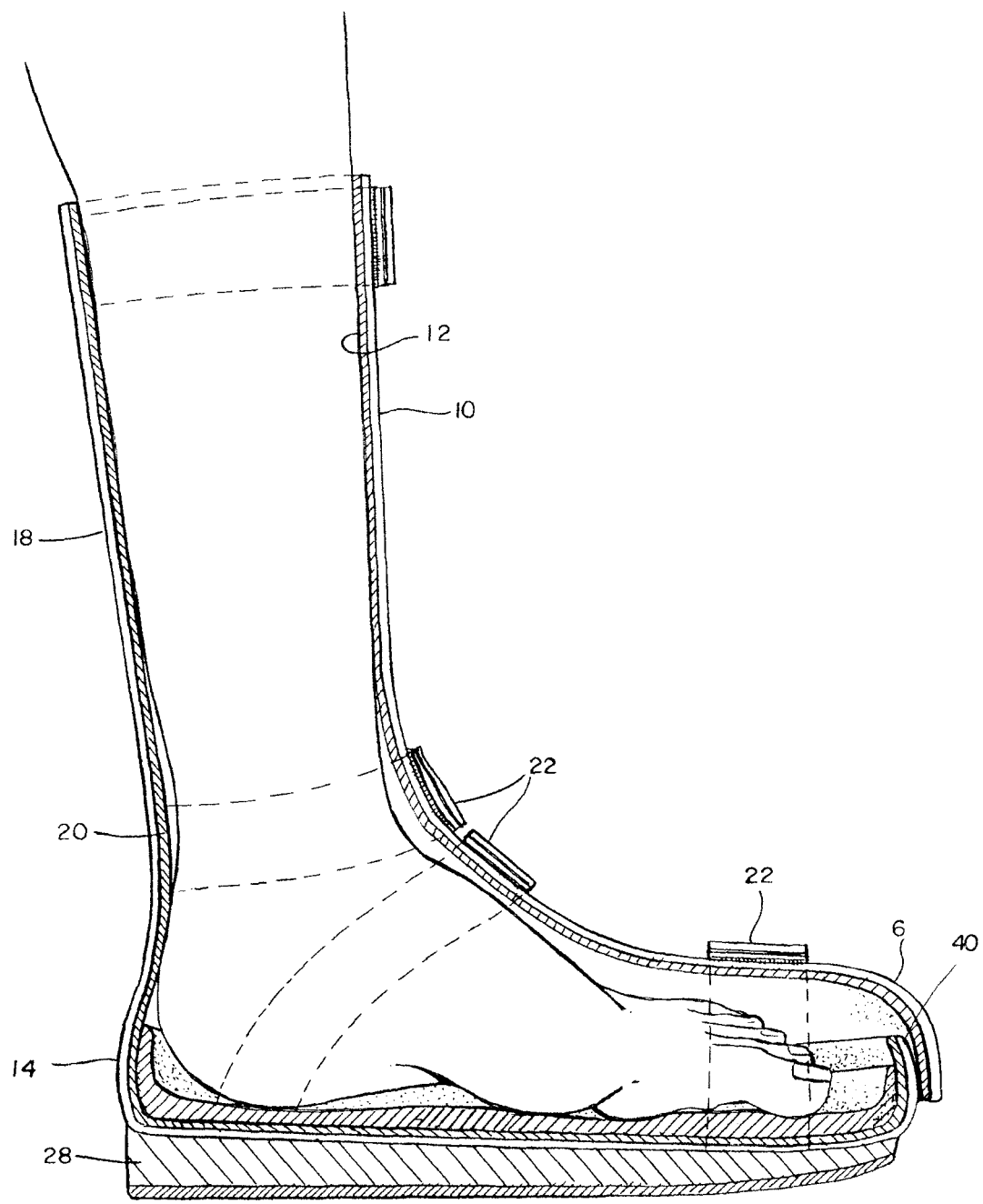
FIG. 2 is a cross sectional view of the orthosis walking boot attached to a patient suffering from Charcot disease with edema in the ankle/foot area.

The V side openings 9 are configured to permit a first portion of the first leg covering 10 to be inserted directly against an internal surface of the posterior shell 14 while the anterior foot covering 6 is also configured to extend over and enclose a foot opening 7, as shown in FIG. 2, that illustrates a user or patient's foot.

Figure 8:
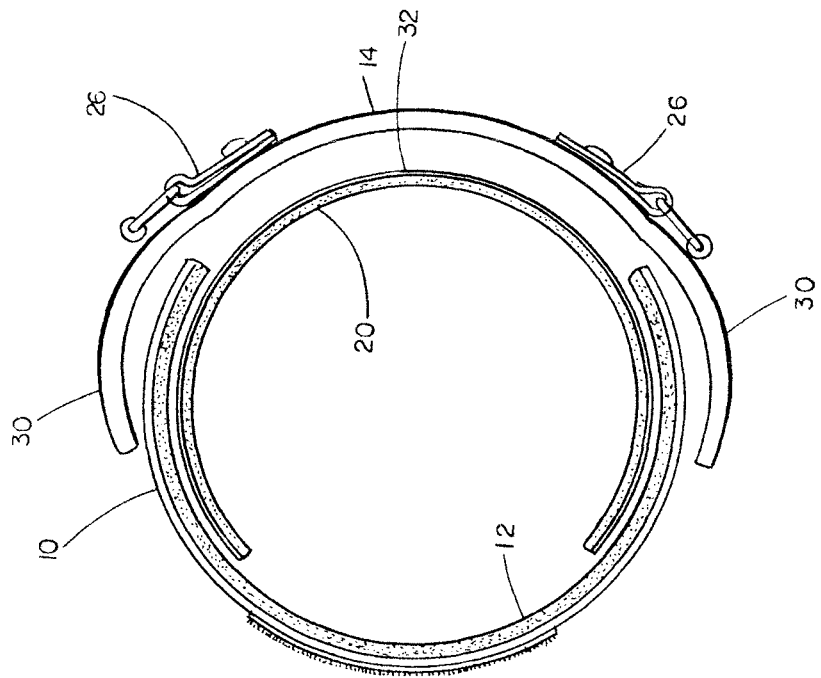
FIG. 8 is a schematic top view of a relationship between the flexible anterior shell and the more rigid posterior shell.

With reference to FIG. 3, a foam posterior liner 20 can be a copolymer of ethylene-vinyl acetate (EVA) and provides a bottom covering on the interior of the posterior shell 14. An additional foam insert 21 can be provided immediately above the foam posterior lining 20 to contact the bottom of the patient's foot and can be reconfigured to address any foot issues such as swelling or ulcer sores. As can be seen in FIG. 3 and FIG. 8, a first foam embodiment of an EVA foam posterior lining 20 extends upward within the upward extension of the posterior shell 18 in a relatively loose manner that is not bound or affixed to the upward extension 18. The foam posterior lining 20 can extend upward above a top edge of the posterior shell 14 as seen in FIG. 1. Additionally, as seen in FIG. 3, a trim line of the foam posterior liner 20 extends forward beyond the front edges of the upward extension of the posterior shell 18 to facilitate an entrance of the front leg covering 10. The foam posterior liner 20 has an outer layer of 22 pound density of EVA to provide support while the inner layer of EVA has a 5 pound density to contact the patient with a soft foam.

This arrangement of the foam posterior liner 20 facilitates an introduction of the respective sides of the anterior front leg covering 10 so that the outer plastic shell of the anterior shell 4 can bear directly against an interior surface of an upward extension of the posterior shell 18 to assure that the foam lining 20 can be positioned within an affixed anterior foam liner 12 on the anterior leg covering shell 10. An example of an applicable foam for the liner 12 can be a Volara® polyethylene foam that can be purchased, for example, with an adhesive glue for affixing to both an interior curved surface of the front vertical leg covering 10 and the anterior foot covering portion 6. Volara® which can be purchased as a polyolefin-based polyethylene foam from Sekisui Voltec LLC having a closed cell configuration with virtually microscopic cells to provide an extremely soft texture with a consistent thickness/texture/density and a relatively high tensile strength, low water absorption and vapor transmission.

Figure 10:
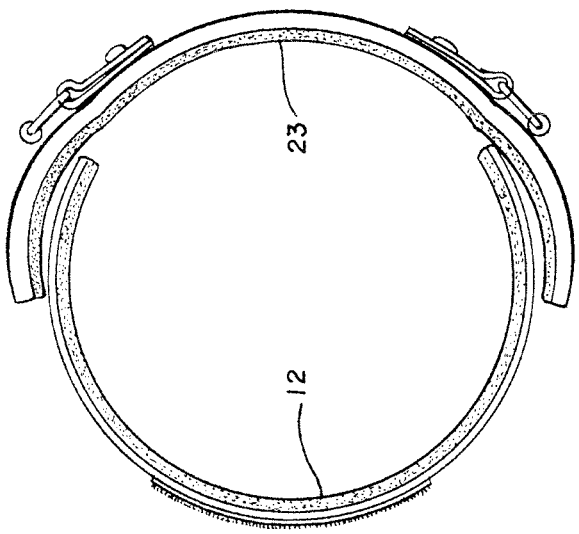
FIG. 10 is a schematic top view of a relationship between the flexible anterior shell and the more rigid posterior shell with respective integrally attached foam liners.
Figure 9:
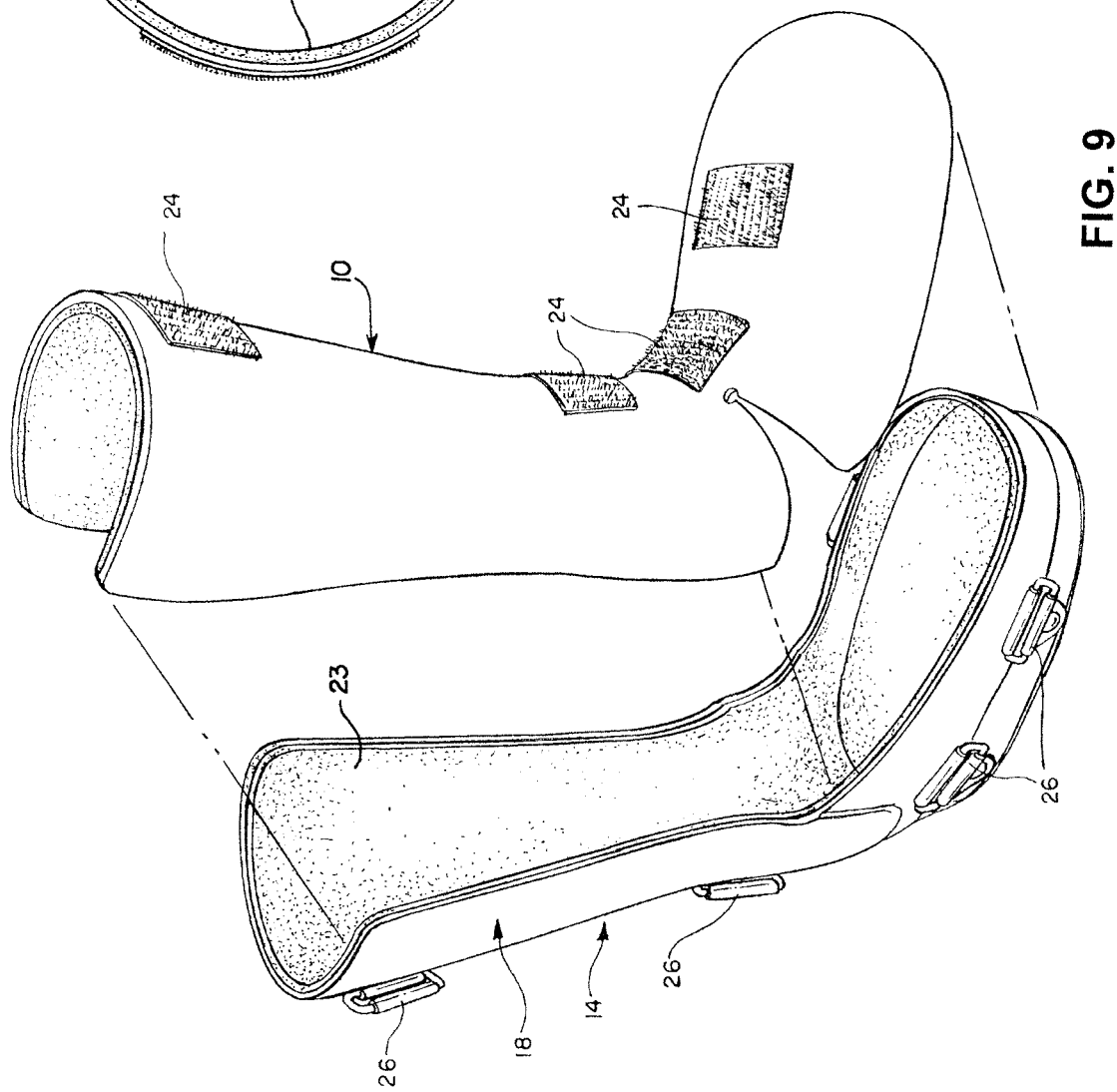
FIG. 9 is an exploded view of another embodiment of the orthosis walking boot with an interior of both the posterior shell and the anterior shell having integrally attached foam liners.

A second embodiment of an orthosis walking boot 2 where a foam posterior liner 23 can be laminated on the interior of the upward extension 18 of the posterior shell 14 can be seen in FIGS. 9 and 10. Thus, depending on the circumstances of the patient, the orthotist can select either the free standing foam liner 20 arrangement shown in FIGS. 1, 3 and 8 or the laminated foam posterior liner 23 shown in FIGS. 9 and 10.

Figure 4:
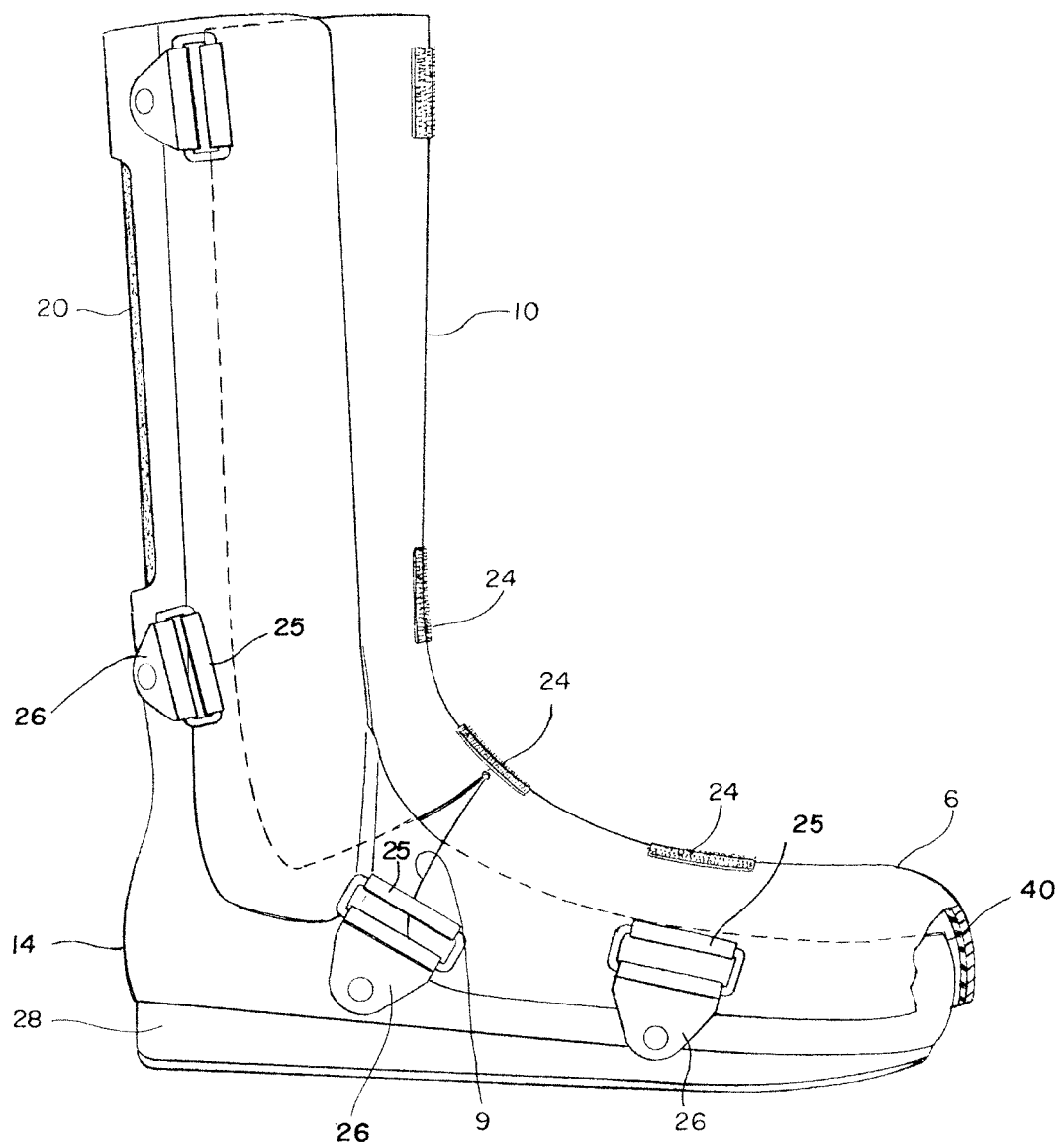
FIG. 4 is a side view of an assembled relationship of the anterior shell and the posterior shell without the straps.

A plurality of rectangular segments 24 of one of a hook and nap material such as Velcro® can be adhered to a front surface of the anterior shell 4, as seen in FIG. 3. As disclosed, hook material is disclosed in our drawings but nap material could be utilized. The segments 24 have an adhesive on a rear surface for a firm securement to the anterior shell 4. A set of four braces 26 have a size sufficient to receive and pass the straps 22 to set the desired positions of the posterior shell 14 and the anterior shell 4. As seen in FIG. 2, anterior foot covering 6 can be affixed to the posterior shell 14. A set of four braces 26 are attached on the respective left and right hand side of the posterior shell 14, as seen in FIGS. 3 and 4. Each of the braces 26 can support a roller 25 of a size and dimension to receive and permit smooth movement of the flexible straps 22 for tightening the anterior shell 4 so that the anterior foot covering 6 can be independently positioned and tightened to meet the demands of the patient's foot. Likewise, the braces 26 that extend outward from an upward extension of the posterior shell 18 can receive a strap 22 and permit a subjective tightening in an effort to transfer weight to a patient's lower leg and reduce the weight on the bottom of the foot of a patient. The segments 24 can be either of a nap or hook configuration to facilitate locking the straps 22 to the front of the anterior shell 4. As shown for example in FIG. 3, the segments 24 of a rectangular configuration are a hook material.

The braces 26 are not only dimensioned to freely permit the straps 22 to pass through as far as width and thickness of the straps 22, but further have a roller 25 in the form of a free rolling cylinder to further facilitate tightening the straps 22 by using the leverage of the straps 22 extending through the braces 26.

The bottom of the posterior shell 14 has a sole 28, of rubber or similar material, that is permanently fastened to the bottom of the posterior shell 14. The outer edges of the vertically upwardly extending posterior shell 18 has concave edges 30 that extend somewhat outward for facilitating an insertion of the anterior front leg covering 10, see the top view of FIG. 8. As can be seen in FIG. 3 and FIG. 8, this indent extends for substantially the length of the edges 30 of the upward extension 18 of the posterior shell 144 and is configured to accommodate the outer edges of the anterior front leg covering 10.

The foam posterior liner 20 includes a thin relatively more dense outer surface 32 that can support the foam interior liner 20 that will contact the patient's leg. This arrangement permits the relatively dense surface 32, shown in FIG. 8, to maintain an open configuration and further facilitates the insertion of the anterior front vertical leg covering 10 into the upward extension 18 of the posterior shell 14.

Also assisting the nesting of the anterior front leg covering 10 into the upward extension 18 of the posterior shell 14 is the manner in which the foam posterior liner 20 extends beyond and forward of a trimline of the posterior extension 18 of the posterior shell 14 as seen in FIG. 3. This arrangement facilitates an internal mounting of the front leg covering 10 into the posterior upward extension 18. Additionally, because of the split hinge 8 and its peripheral openings 9, our orthosis walking boot 2 provides some freedom in adjusting a height of the anterior foot covering 6 separate from the securement of the front leg covering 10 within the posterior shell 14. As shown in FIG. 1, the upper strap 22 adjacent the upper opening enables the patient's upper calf to be comfortably surrounded with foam linings 20 and 12 while the straps 22 permit a sufficient tightening to transfer a portion of the patient's weight, that is usually supported by the foot, from the user's calf down to the sole 28 of the orthosis walking boot 2.

Likewise, the lower strap 22 on the front leg covering 10 also permits some weight of the patient to be transferred again to the sole 28 as opposed to exerting a force through the inflamed foot, as shown in FIG. 2, that is now protected within the posterior foot opening 7.

Figure 5:
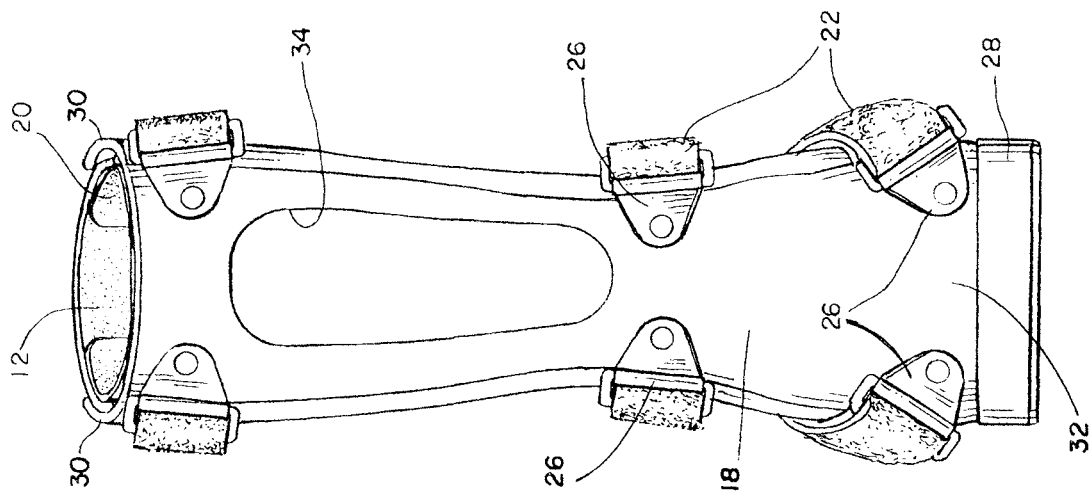
FIG. 5 is a rear view disclosing the relationship of the anterior hard shell and the posterior hard shell along with the foam and an oval opening through the back of the posterior hard shell.

Referring to FIG. 5, a back perspective of the orthosis walking boot 2 is disclosed with the oblong opening 34 extending through the upward extension 18 of the posterior shell 14 with a rear surface of the semi-rigid base 32 shown.

As can be determined, the oblong opening 34 not only lightens the boot, it still provides sufficient strength while contributing some flexibility to the upper portion or upward extension 18 of the posterior shell 14 to accommodate the tightening of the straps 22. It also permits the orthotist to localize an application of heat for any size adjustments on the posterior upper portion of the shell 14 and the lower portion below the oblong opening 34, since there is less plastic to receive heat from the heat gun.

Figure 6:
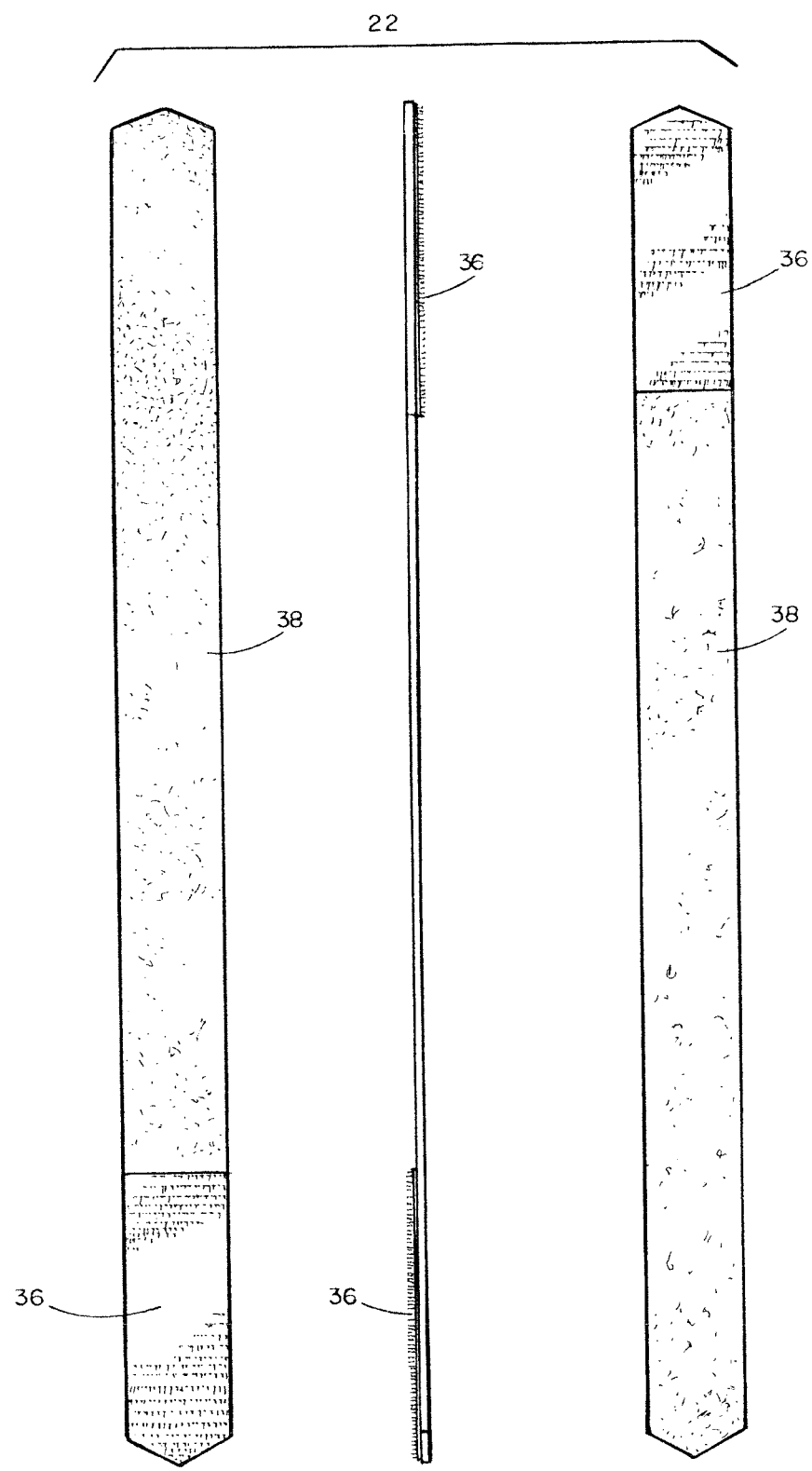
FIG. 6 discloses a relationship of fastening nap and hook sections of the individual straps.

The straps 22 shown in FIG. 6 are arranged with combinations of hook portions 36 and nap portions 38 to facilitate looping the strap 22 to affix it to one of the braces 26 and threading the strap 22 through the opposite side brace 26 so that the rollers 25 facilitate pulling a strap 22 back across and tightening it with the nap 36 at the end of the strap 22 by fastening to the hooks on the other side of the same strap. The rectangular hook segments 24 provide another direct anchor point on the anterior shell 4 for the respective straps 22.

Figure 7:
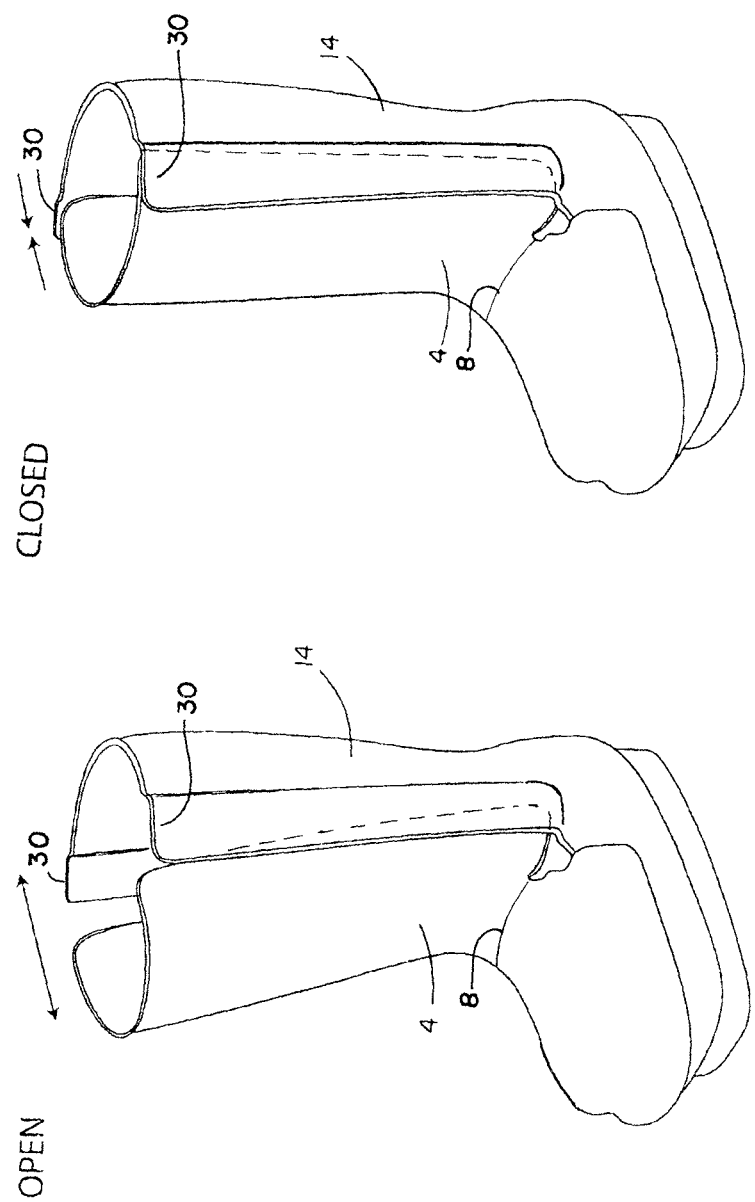
FIG. 7 discloses a comparison between an open and closed configuration for the orthosis walking boot.

Referring to FIG. 7, a view of the anterior shell 4 is shown schematically in an open position for an insertion into the posterior shell 14. The closed position of FIG. 7 shows a relationship of the anterior and posterior shells in a closed condition as an illustration.

In FIG. 2, a patient with a swollen edema is shown mounted with an orthosis walking boot 2 with the anterior foot covering 6 appropriately mounted over posterior side wall perimeter 40 of the sole to provide space for the swollen foot and further encapturing the posterior foot opening 7 to provide protection for the patient.

The orthosis walking boot 2 can serve the patient not only at the initial treatment of the Charcot Syndrome but also as the foot is being successfully treated so that the edema is being reduced and the same orthosis walking boot 2 can then be adjusted to accommodate the comfort of the patient with an appropriate sizing between the anterior shell 4 and the posterior shell 14 as described above.

While the above features of the present invention teach apparatus, process and an improved orthosis walking boot, it can be readily appreciated that it would be possible to deviate from the above embodiments of the present invention and, as will be readily understood by those skilled in the art, the invention is capable of many modifications and improvements within the scope and spirit thereof. Accordingly, it will be understood that the invention is not to be limited by the specific embodiments but only by the spirit and scope of the appended claims.

What is claimed is:

1. An orthosis walking boot comprising:
   a posterior shell with an open horizontal lower foot supporting portion extending outward from an open vertical leg extension configured to support a muscular back of a user's leg above the user's foot and below the user's knee;
   an anterior shell with a horizontal foot covering portion of a size to overlap and cover a foot and the lower foot supporting portion of the posterior shell to enclose and protect the user's foot and toes during walking and an integral open vertical leg extension configured to extend upward from the horizontal foot covering portion to support a front part of a user's leg, wherein the integral open vertical leg extension is dimensioned to slide within the open vertical leg extension of the posterior shell; and
   adjustable fastening units to secure a relative location of the posterior shell to the anterior shell on a user, wherein the anterior shell include a hinge which enables relative movement between the horizontal foot covering portion and the integral open vertical leg extension, wherein a curved V opening is provided through the anterior shell on each side of the hinge to inhibit any cracking of the anterior shell adjacent the hinge.

2. The orthosis walking boot of claim 1 wherein the anterior shell has openings extending from either side of the hinge to a perimeter of the lower anterior foot covering to facilitate relative movement and enable the rear edges of the hinge to extend within the posterior shell.

3. The orthosis walking boot of claim 2 wherein the anterior shell has a foam interior liner affixed to a rear surface of the anterior shell.

4. The orthosis walking boot of claim 3 wherein the posterior shell has a foam interior liner affixed to an interior surface of the posterior open vertical leg extension.

5. The orthosis walking boot of claim 1 wherein the posterior shell has a free standing foam posterior liner extending upward within the posterior open vertical leg extension.

6. The orthosis walking boot of claim 5 wherein the free standing foam posterior liner is mounted within the integral open vertical leg extension to enable the anterior shell integral open vertical leg extension to extend adjacent an interior of the posterior shell open vertical leg extension with the free standing foam posterior liner extending within the vertical leg extension of the anterior shell for contact with a user's leg.

7. The orthosis walking boot of claim 5 wherein the posterior shell foam posterior liner has a denser exterior layer as a support structure and a less dense interior foam layer for contacting the user, the posterior shell foam posterior liner is not fastened to the posterior shell within the open vertical leg extension.

8. The orthosis walking boot of claim 1 wherein the anterior shell horizontal foot covering portion has a cross sectional U shape that extends over a relative rigid side wall of the posterior shell foot supporting portion that forms a perimeter above the sole.

9. The orthosis walking boot of claim 1 wherein the adjustable fastening units include braces with movable rollers fixed to an exterior of the posterior shell and flexible straps that can extend across a surface of the anterior shell and be secured to fasten the anterior shell to the posterior shell.

10. The orthosis walking boot of claim 1 wherein the posterior open vertical leg extension has an oblong elongated opening extending vertically through a rear surface.

11. The orthosis walking boot of claim 10 wherein the side edges of the front of the posterior open vertical leg extensions are curved outwardly to receive the edges of the anterior shell integral open vertical leg extension to enable compression adjustments to accommodate edema fluctuations in the user's leg.

12. The orthosis walking boot of claim 1 wherein the posterior shell is formed of a plastic of sufficient thickness to be relatively rigid and the anterior shell is formed of a plastic of sufficient thickness to be more flexible than the posterior shell.

13. The orthosis walking boot of claim 12 wherein the plastic posterior shell is at least twice as thick as the anterior shell.

14. An orthosis walking boot comprising:
a posterior shell with an open horizontal lower foot supporting portion extending outward from an open vertical leg extension configured to support a muscular back of a user's leg above the user's foot and below the user's knee;
a two layer foam posterior liner with a denser exterior layer is attached to the open horizontal lower foot supporting portion and a less dense interior foam layer for contacting the user, wherein the two layer foam posterior layer extends upward within the open vertical leg extension without any direct attachment to the open vertical leg extension of the posterior shell;
an anterior shell with a horizontal foot covering portion of a size to overlap and cover the lower foot supporting portion of the posterior shell and an integral open vertical leg extension configured to extend upward from the horizontal foot covering portion to support a front part of a user's leg, wherein the integral open vertical leg extension is dimensioned to slide within the open vertical leg extension of the posterior shell;
a hinge interconnects the horizontal foot covering and the integral open vertical leg extension wherein a curved V opening is provided through the anterior shell on each side of the hinge to inhibit any cracking of the anterior shell adjacent the hinge;
a single layer foam anterior liner is attached to the interior of the anterior shell within the horizontal foot covering portion and the integral open vertical leg extension, the single layer foam anterior liner is thicker than the posterior two layer foam liner; and
adjustable fastening units to secure a relative location of the posterior shell to the anterior shell on a user.

* * * * *